United States Patent [19]

Andress et al.

[11] Patent Number: 5,006,272
[45] Date of Patent: Apr. 9, 1991

[54] FRICTION REDUCING ADDITIVES AND COMPOSITIONS THEREOF

[75] Inventors: Harry J. Andress, Wenonah; Andrew G. Horodysky, Cherry Hill; Joan M. Kaminski, Clementon, all of N.J.

[73] Assignee: Mobil Oil Corporation, Fairfax, Va.

[21] Appl. No.: 415,418

[22] Filed: Sep. 29, 1989

Related U.S. Application Data

[63] Continuation of Ser. No. 249,245, Sep. 22, 1988, abandoned, which is a continuation of Ser. No. 763,778, Aug. 9, 1985, abandoned, which is a continuation of Ser. No. 133,034, Mar. 24, 1980, abandoned.

[51] Int. Cl.$^5$ .......................................... C10M 105/78
[52] U.S. Cl. ................................. 252/49.6; 252/46.4; 260/398; 260/399; 260/405; 260/405.5; 558/251; 558/252; 558/253; 558/255; 558/285; 558/296
[58] Field of Search ............................ 252/46.4, 49.6; 260/462, 398, 399, 405, 405.5; 558/230, 236, 251, 252, 253, 255, 285, 296

[56] References Cited

U.S. PATENT DOCUMENTS

| | | | |
|---|---|---|---|
| 2,090,756 | 8/1937 | Hansen et al. | 538/230 X |
| 2,499,983 | 3/1950 | Beavers | 252/49.6 X |
| 2,795,548 | 6/1957 | Thomas et al. | 252/49.6 |
| 2,950,250 | 8/1960 | Fainman | 252/49.6 |
| 3,117,089 | 1/1964 | DeYoung et al. | 252/46.7 |
| 3,151,077 | 9/1964 | Liao | 252/49.6 |
| 3,235,499 | 2/1966 | Waldmann | 252/49.6 |
| 3,509,054 | 4/1970 | Hinkamp et al. | 252/49.6 |
| 3,533,945 | 10/1970 | Vogel | 252/49.6 |
| 4,107,385 | 8/1978 | Higuchi et al. | 428/412 |
| 4,370,248 | 1/1983 | Horodysky et al. | 252/49.6 |

FOREIGN PATENT DOCUMENTS

| | | | |
|---|---|---|---|
| 36708 | 9/1981 | European Pat. Off. | |
| 1295877 | 11/1972 | United Kingdom | 252/47.6 |

OTHER PUBLICATIONS

Chemical Abstracts, vol. 75(1971), 63112m.
Chemical Abstracts, vol. 81(1974), 128992q.
Chemical Abstracts, vol. 81(1974), 153669x.
Chemical Abstracts, vol. 82(1975), 47631q.
Chemical Abstracts, vol. 83(1975), 207485w.
Chemical Abstracts, vol. 88(1978), 38553n.
Chemical Abstracts, vol. 88(1978), 16234m.
Chemical Abstracts, vol. 89(1978), 216341x.
Chemical Abstracts, vol. 90(1979), 123486d.
Chemical Abstracts, vol. 93(1980), 238852z.
J 5 2102-362 (Japanese Abstract) 1977.
J 7 8039-413 (Japanese Abstract), 1978.
J 7 4011-311 (Japanese Abstract), 1974.
J 7 343371 (Japanese Abstract), 1973.
Booser, CRC Handbook of Lubrication (Theory and Practice of Tribology), vol. II, CRC Press, Florida (1988) pp. 3-67, 301-309, 324-339, 463-467, 477-481, 488-494, 524, 543-545 & 558-563.
SAE Technical Paper Series No. 830166, *Improving the Fuel Saving Benefits of Synthetic Engine Oils*, H. V. Lowther et al. (SAE, Feb. 1983).
SAE Technical Paper Series No. 800436, *The Performance of Fuel-Saving Engine Oils*, J. R. Lohuis et al. (SAE, Feb. 1980).
*Lubrication*, R. C. Gunther, Chilton Book Co., Philadelphia, pp. 256-261, 268-271, Table 10-3.
*The Performance of Lubricating Oils*, H. H. Zuidema, American Chemical Society, Washington, D.C., pp. 2-9, 172-175.
*Lubricants and Related Products*, D. Klamann, Verlag Chemie, Weinheim, pp. 203, 208-215.
*Lubrication in Practice*, W. S. Robertson (Ed.), Marcel Dekker, New York, p. 108.
*Lubrication A Practical Guide to Lubricant Selection*, A. R. Lansdown, Pergamon Press, Oxford, pp. 44-45.

*Primary Examiner*—Richard L. Raymond
*Attorney, Agent, or Firm*—Alexander J. McKillop; Charles J. Speciale; Jessica M. Sinnott

[57] ABSTRACT

Borated glycerol hydroxyesters are effective friction reducing additives when incorporated into lubricating compositions.

19 Claims, No Drawings

FRICTION REDUCING ADDITIVES AND COMPOSITIONS THEREOF

This is a continuation of application Ser. No. 249,245, filed on Sept. 22, 1988, now abandoned, which is a continuation of application Ser. No. 763,778, filed on Aug. 9, 1985, now abandoned, which is a continuation of application Ser. No. 133,084, filed on Mar. 24, 1980, now abandoned.

BACKGROUND OF THE INVENTION

1. Field of the Invention

This invention relates to lubricant additives and compositions thereof and, more particularly, to lubricant compositions comprising oils of lubricating viscosity or greases prepared therefrom containing a minor friction reducing amount, of a borated glycerol hydroxy-ester.

2. Background of the Related

Many means have been employed to reduce overall friction in modern internal combustion engines, particularly automobile engines. The primary reasons are to reduce engine wear thereby prolonging engine life and to reduce the amount of fuel consumed by the engine thereby reducing the engine's energy requirements or fuel consumption.

Many of the solutions to reducing fuel consumption have been strictly mechanical, as for example, setting the engines for a leaner burn or building smaller cars and smaller engines. However, considerable work has been done with lubricating oils, mineral and synthetic, to enhance their friction properties by modifying them with friction reducing additives.

Glycerol hydroxyesters may be used for their friction reducing properties when added to lubricant fluids. However, glycerol hydroxyesters do not adequately control bearing corrosion when used in automotive engine oil lubricants possibly because of their reactive OH groups. Borated glycerol hydroxyesters and borated sulfur containing hydroxyesters provide better friction reduction than their unborated counterparts and, in addition, reduce bearing corrosion to minimal, acceptable levels. The borated glycerol esters of the present invention to the best of applicants' knowledge and belief are novel and have not been used as friction reducing additives or as anti-corrosion or antioxidant additives in lubricating compositions.

SUMMARY OF THE INVENTION

This invention is directed to novel additive compounds, i.e., borated derivatives of glycerol hydroxyesters and borated derivatives of sulfur-containing glycerol hydroxyesters. The glycerol or thioglycerol hydroxyesters have the following generalized structural formulae:

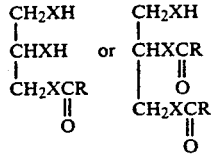

where X is S or O and R contains from about 8 to 24 carbon atoms. In addition to these novel compounds the invention is also directed to lubricant compositions having reduced friction containing such compounds and to a method of reducing fuel consumption in internal combustion engines by treating the moving surfaces thereof with said compositions. Further the novel additive compounds referred to herein above also possess significantly improved antioxidant characteristics and bearing corrosion inhibiting properties.

DESCRIPTION OF SPECIFIC EMBODIMENTS

The borated derivatives of the present invention are produced by the reaction of a glycerol hydroxyester with boric acid in a suitable solvent or solvents at temperatures ranging from about 90° C. to about 280° C. to yield products containing at least 0.01% or more of boron. Specific reaction conditions and molar equivalents of the reactants are well known in the art. Partial or complete boration can be used to impart the beneficial characteristics. An excess of a boron-containing borating reagent can be used. More complete boration is generally preferred. Boration is not limited to the boric acid method, however, any convenient method of boration known to the art may be used. For example, transesterification using a trialkyl borate such as tributyl borate at reaction temperatures up to 270° C.

The glycerol hydroxyesters and thioglycerol hydroxyesters may be prepared by any means known to the art or may be obtained commercially. A non-exhaustive list of glycerol hydroxyesters and thioglycerol hydroxyesters useful herein include glycerol monooleate, glycerol dioleate, monothioglycerolmonooleate, monothioglycerol dioleate, dithioglycerolmonooleate, dithioglycerol dioleate, trithioglycerolmonooleate, trithioglycerol dioleate, glycerol monoricinoleate, glycerol diricinooleate, and in general, mono- and diesters of glycerol or mono-, di-, and trithioglycerol such as glycerol laurates, etc. and mono-and diesters such as glycerol laurates, myristates, palmitates, stearates, phenyl stearates, and unsaturated analogs thereof. Diglycerol di(thioglycerol) partial esters of diacids, yielding for example diglycerol adipates or sebacates, are other types of hydroxyesters included herein. Mixtures and various combinations of the above-listed hydroxyesters and thiohydroxyesters are also useful herein.

Thus pure esters or mixtures of esters such as a 60/40 mixture of glycerol monooleate/glycerol dioleate may be borated. Mixtures can, on occasion, be preferable to the use of pure esters. The amount of additive required to be effective in lubricant compositions may range from 0.1 to about 10% by weight of the total lubricant composition. Preferred is from about 0.5 to about 5 wt. %. The additives of this invention may be used in combination with any conventional additive for its known purpose, e.g., dispersants, surfactants, antiwear agents, in amounts of up to about 10 wt. %.

The lubricants contemplated for use herein include both mineral and synthetic hydrocarbon oils of lubricating viscosity, mixtures of mineral and synthetic oils, and greases or other solid lubricants prepared therefrom. The synthetic hydrocarbon oils include long chain alkanes such as cetanes and olefin polymers such as trimers and tetramers of long chain 2-olefins. These synthetic oils can be mixed with other synthetic oils which include (1) ester oils such as pentaerythritol esters of monocarboxylic acids having 2 to 20 carbon atoms, (2) polyglycol ethers, (3) polyacetals and (4) siloxane fluids. Especially useful among the synthetic esters are those made from polycarboxylic acids and monohydric alcohols. More preferred are the ester fluids made from pentaerythritol, and an aliphatic monocarboxylic acid containing from 1 to 20 carbon atoms, or mixtures of such acids. Having described the invention in general terms, the following are offered as specific illustrations thereof. It is to be understood they are illustrations only and that the invention is not thereby limited except as by the appended claims.

EXAMPLE 1

Synthesis of Monothioglycerol Monooleate

A mixture of 1-thioglycerol (70.5 g), 2-pentanone (277 g), and p-toluene sulfonic acid (2 g) was refluxed until the expected 20 cc. of water formed and was azeotroped off. Oleic acid (163 g) was added to the reaction solution which was then refluxed until the expected 10 cc. of H2O azeotroped off. Toluene (800 cc.) was added to the cooled reaction solution, which was then shaken with sodium acetate (6 g), washed with H2O (4 x 400 cc.) and dried over sodium sulfate. The toluene solution was filtered and the solvents removed via high speed rotary evaporation under reduced pressure. The resulting yellow fluid (190 g) was refluxed in monomethyl ethylene glycol (520 cc.) with boric acid (103 g) at 100° C. for 2 hours. Ether was added (875 cc.) and the entire solution was transferred to a separatory funnel, washed with water (4 x 750 cc.), washed with 13% sodium bicarbonate solution (2 x 100 cc.) and washed with water (2 x 100 cc.). The ether solution was shaken with sodium acetate (14 g) and 100 cc. of water and then washed with a saturated sodium chloride solution (3 x 150 cc.). The ether solution was dried over magnesium sulfate, stripped free of solvent, and filtered through diatomaceous earth to yield a clear bright yellow oil. Gel permeation chromatography showed that the product was acid free (oleic) and contained approximately 80% monothioglycerol monooleate and 20% monothioglycerol dioleate.

EXAMPLE 2

Borated Monothioglycerol Monooleate

A mixture of monothioglycerol monooleate (214 g), boric acid (24 g), and n-butanol (127 g) was refluxed at 100 to 140° C. until the theoretical amount of water, expected to form in the reaction, azeotroped off. The n-butanol was distilled off under vacuum, and the resulting product residue was filtered yielding a clear, orange liquid.

EXAMPLE 3

Borated Monothioglycerol Monooleate

Monothioglycerol monooleate was borated in a manner identical to that of Example 2 except that the reaction was allowed to proceed until 80% of the expected water azeotroped off. The unreacted boric acid was filtered, and the n-butanol was distilled off under vacuum. The resulting product was a clear orange fluid.

EXAMPLE 4

Glycerol Monooleate obtained commercially

EXAMPLE 5

Borated Glycerol Monooleate

A mixture of glycerol monooleate (1900 g), boric acid (165 g), and n-butanol (200 g) was refluxed at 140° C. for 6 hours and 250° C. for 6 hours until all the water formed in the reaction had azeotroped off and solvent distilled over. No insolubles were visible in the resulting pale orange liquid product.

EXAMPLE 6

Borated Glycerol Monooleate (Using Excess Boric Acid)

A mixture of glycerol monooleate (1158 g), boric acid (202 g), and n-butanol (300 g) was refluxed at 275° C. for 6–7 hours until all the water and solvent had been removed. Filtration yielded a pale orange liquid product.

EXAMPLE 7

A mixture of glycerol monoricinoleate (42 g), boric acid (6.9 g), and n-butanol (106 g) were refluxed at 105–140° C. until all water formed in the reaction had azeotroped over. Solvent was distilled off under reduced pressure at 175° C. The resulting rust-colored, very viscous product was sparingly soluble in mineral oils.

Each of the above examples was then individually incorporated into a fully formulated 5W-20 engine oil having the following general characteristics; KV @100° C. - 6.8 cs; KV @40° C. - 36.9 cs; VI - 143 and evaluated using the Low Velocity Friction Apparatus. Certain of the examples were also subjected to the CRC L-38 Bearing Corrosion Test, which is a well-known test, utilizing herein a single-cylinder, spark-ignited engine and which is designed to determine bearing corrosion and deposit forming characteristics of lubricants under high temperature oxidation conditions.

Low Velocity Friction Apparatus (LVFA)

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in. $^2$). Both surfaces are submerged in the test lubricant. Friction between the steel surfaces is measured as a function of the sliding speed at a lubricant temperature of 250° F. The friction between the rubbing surfaces is measured using a torque arm strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½HP electric motor. To vary the sliding speed, the output speed of the transmission is regulated by a lever cam-motor arrangement.

Procedure

The rubbing surfaces and 12–13 ml. of test lubricant are placed on the LVFA. A 500 psi load is applied, and the sliding speed is maintained at 30 fpm at ambient temperature for a few minutes. A plot of coefficients of friction ($U_k$) over a range of sliding speeds, 5 to 40 fpm (25–195 rpm), is obtained. A minimum of three measurements is obtained for each test lubricant. Then, the test lubricant and specimens are heated to 250° F., another set of measurements is obtained, and the system is run for 50 minutes at 250° F., 500 psi, and 40 fpm sliding speed. Freshly polished steel specimens are used for each run. The surface of the steel is parallel ground to 4 to 8 microinches. The percentages by weight are percentages by weight of the total lubricating oil composition, including the usual additive package. The data are percent decrease in friction according to:

$$\frac{(U_k \text{ of oil alone}) - (U_k \text{ of Additive plus oil})}{(U_k \text{ of oil alone})} \times 100$$

The value for the oil alone would be zero as shown in the Table below.

TABLE

Results Using LVFA

| Additive | Conc. (Wt. %) | % Change in Coefficient of Friction in LVFA at | |
|---|---|---|---|
| | | 5 Ft./Min. | 30 Ft./Min. |
| Base Fluid[a] | — | 0 | 0 |
| Base Fluid plus Example 1, monothioglycerol monooleate | 4 | −5 | −1 |
| Base Fluid plus Example 2, borated monothioglycerol monooleate | 4 | 41 | 33 |
| | 2 | 28 | 14 |
| Base Fluid plus[b] Example 3, borated monothioglycerol monooleate (Partially Borated) | 4 | 20 | 18 |
| | 2 | 18 | 12 |
| | 1 | 16 | 16 |
| Base Fluid plus Example 4, glycerol monooleate[c] | 4 | 21 | 22 |
| | 2 | 15 | 17 |
| Base Fluid plus Example 5, borated glycerol monooleate | 2 | 40 | 30 |
| Base Fluid plus Example 6, borated glycerol monooleate[b] (excess boric acid used) | 4 | 25 | 16 |
| Base Fluid plus Example 7, borated glycerol monoricinoleate | 2 | 18 | — |

[a] A fully formulated engine oil consisting of base fluid and 20% by weight of an additive package containing antioxidant, detergent, and dispersant, having the following general characteristics: KV @ 100° C. - 6.8 cs; KV @ 40° C. - 36.9 cs; VI - 143
[b] Passed L-38 bearing corrosion test after 80 hrs.
[c] Failed L-38 bearing corrosion test after 40 hrs.

The test data establishes that the borated hydroxyesters and borated sulfur containing hydroxyesters are more efficient friction reducers than their non-borated counterparts. A significant reduction in the coefficient of friction was observed relative to the base oil or the base oil containing the non-borated monothioglycerol monooleate or glycerol monooleate. Furthermore, these borated derivatives retain anti-friction behavior at low concentrations, i.e., 1% and 2% by weight. Also, the boration provides protection against bearing corrosion thereby imparting multifunctional additive properties to the borated glycerol esters while the non-borated glycerol hydroxyesters failed the L-38 test after only 40 hours.

It is understood that departures and variations from the exemplary matter disclosed herein can be readily made by one of ordinary skill in the art and is within the scope of the present specification and claims.

We claim:

1. A method for reducing friction in an internal combustion engine, using a friction reducing borated additive in a lubricant composition, comprising:
lubricating moving surfaces of the engine with a lubricating composition which includes a lubricant oil and a friction reducing borated additive in a concentration of at least 1% by weight of the lubricating composition, said friction reducing borated additive includes a borated glycerol mono- and/or dihydroxyester or borated thioglycerol mono and-/or dihydroxyester produced by borating a glycerol mono and/or dihydroxyester or thioglycerol mono-and/or dihyroxyester of the formula:

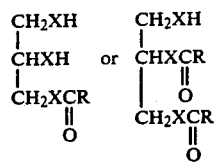

2. The method recited in claim 1, wherein X is oxygen and R contains 17 carbon atoms.

3. The method recited in claim 1, wherein X is sulfur and R contains 17 carbon atoms.

4. The method recited in claim 1, wherein the glycerol hydroxyester is a mixture of monohydroxy and dihyroxy esters.

5. The method recited in claim 4, wherein the glycerol hydroxyester is a 60/40 mixture of glycerol monooleate and glycerol dioleate.

6. The method recited in claim 1, wherein the lubricant is a grease prepared from a mineral or synthetic hydrocarbon oil of lubricating viscosity or a mixture of mineral and synthetic oils.

7. In a method of lubricating an internal combustion engine by applying a lubricating composition to relatively moving surfaces of the engine, the improvement comprising reducing the friction between the moving surfaces by the use of a composition which includes a lubricating oil and a friction reducing borated glycerol mono and/or dihydroxyester or a borated thioglycerol mono and/or dihydroxyester obtained by borating a glycerol mono and/or dihydroxyester or thioglycerol mono and/or dihydroxyester of the formula:

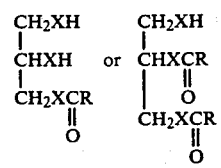

wherein X is S or O and R is a dydrocarbyl group of 8 to 24 carbon atoms.

8. The method recited in claim 7 wherein X is oxygen and R is a hydrocarbyl group of 17 carbon atoms.

9. The method recited in claim 7 wherein X is sulfur and R is a hydrocarbyl group of 17 carbon atoms.

10. The method recited in claim 7 wherein the glycerol hydroxyester is a mixture on monohydroxy and dihydroxy esters.

11. The method recited in claim 7 wherein the glycerol hydroxyester is a 60/40 mixture of glycerol monooleate and glycerol dioleate.

12. In a method of lubricating relatively moving metal surfaces by applying a lubricant composition between the surfaces, the improvement comprising reducing the friction between the relatively moving surfaces by the use of a lubricating composition which includes a lubricating oil and a friction reducing borated glycerol mono and/or dihydroxyester or a borated thioglycerol mono and/or dihydroxyester obtained by borating a glycerol mono and/or dihydroxyester or thioglycerol mono and/or dihydroxyester of the formula:

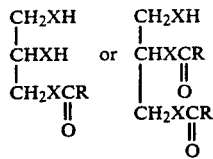

wherein X is S or O and R is a dydrocarbyl group of 8 to 24 carbon atoms.

13. The method recited in claim 12 wherein X is oxygen and R is a hydrocarbyl group of 17 carbon atoms.

14. The method recited in claim 12 wherein X is sulfur and R is a hydrocarbyl group of 17 carbon atoms.

15. The method recited in claim 12 wherein the glycerol hydroxyester is a mixture of monohydroxy and dihydroxy esters.

16. The method recited in claim 12 wherein the glycerol hydroxyester is a 60/40 mixture of glycerol monooleate and glycerol dioleate.

17. The method recited in claim 1, wherein said friction reducing borated additive includes at least 1.49% by weight of boron.

18. The method recited in claim 7 wherein said friction reducing borated additive includes at least 1.49 % by weight of boron.

19. The method recited in claim 12 wherein said friction reducing borated additive includes at least 1.49 % by weight of boron.

* * * * *